United States Patent [19]
Chiu

[11] Patent Number: 5,651,764
[45] Date of Patent: Jul. 29, 1997

[54] PORTABLE APPARATUS FOR REFORMING SPINE

[76] Inventor: Shui-shang Chiu, No. 2, Kokou St., Hsinshih Hsiang, Tainan Hsien, Taiwan

[21] Appl. No.: 610,984

[22] Filed: Mar. 5, 1996

[51] Int. Cl.[6] ........................................................ A61F 5/00
[52] U.S. Cl. ........................ 602/36; 602/19; 602/38; 606/54
[58] Field of Search ............................. 602/5, 19, 32, 602/36, 38; 606/241, 54, 55, 57, 58

[56] References Cited

U.S. PATENT DOCUMENTS

| | | |
|---|---|---|
| 1,316,915 | 9/1919 | Meyer et al. . |
| 1,614,641 | 1/1927 | Anderson . |
| 1,650,650 | 11/1927 | Pieper . |
| 1,722,205 | 7/1929 | Freund . |
| 2,835,247 | 5/1958 | Stabholc . |
| 2,886,031 | 5/1959 | Robbins . |
| 3,420,230 | 1/1969 | Ballard . |
| 3,548,817 | 12/1970 | Mittasch . |
| 3,716,049 | 2/1973 | Kaplan . |
| 3,889,664 | 6/1975 | Heuser et al. . |
| 3,926,182 | 12/1975 | Stabholz . |
| 4,715,362 | 12/1987 | Scott . |
| 4,907,575 | 3/1990 | Satterthwaite . |
| 4,996,978 | 3/1991 | Gingras . |
| 5,195,949 | 3/1993 | Burton et al. . |
| 5,224,924 | 7/1993 | Urso . |
| 5,405,313 | 4/1995 | Albin . |
| 5,462,518 | 10/1995 | Hatley et al. . |

*Primary Examiner*—Linda C. Dvorak
*Attorney, Agent, or Firm*—Morton J. Rosenberg; David I. Klein

[57] ABSTRACT

An apparatus for reforming a spine includes an actuating unit with two recesses respectively defined in each side thereof. Two belts are respectively and securely received in the recesses to enable the actuating unit to be secured round the waist by a belt buckle. A driving device is disposed within the actuating unit. A ram is telescopically fitted to an upper end of the actuating unit and either a chest supporting frame or a cervix traction pole is attached to one end of the ram. The drive device is operated to cause the ram to be moved up and down and the distance between the ram and the actuating unit is changed and thus applies force on the spine to reform the spine.

5 Claims, 7 Drawing Sheets

5,651,764

PORTABLE APPARATUS FOR REFORMING SPINE

FIELD OF THE INVENTION

This invention relates to an apparatus for reforming a spine, and more particularly to an apparatus which is operated easily and has a simple structure.

BACKGROUND OF THE INVENTION

The spine consists of thirty-three vertebrae, which includes seven cervical vertebrae, twelve thoracic vertebrae, five lumbar vertebrae, five sacrum and four coccyx. As is commonly known, if the spine is subjected to a strong external force, it becomes deformed. When the deformation of the spine is such as shown in FIG. 8, once the force is eliminated, the spine can return to normal. If the deformation of the spine is as shown in FIG. 9, even when the force is removed, the spine cannot return to normal and the sufferer must be treated with medical apparatus. However, the sufferer must go to a hospital and spend a lot of time to be treated by the conventional medical apparatus, which is inconvenient.

The present invention provides an improved apparatus for reforming a spine to mitigate and/or obviate the aforementioned problems.

SUMMARY OF THE INVENTION

One object of the present invention is to provide an apparatus for reforming a spine and has a simple structure which is operated easily, whereby the sufferer can be treated at home, without going to hospital.

Another object of the present invention is to provide an apparatus for reforming a spine which can be operated not only electrodynamically but also manually.

According to one aspect of the present invention, an apparatus for reforming a spine includes an actuating unit with two recesses respectively defined in each side thereof, two belts respectively and securely received in a corresponding recess to enable the actuating unit to be secured round the waist by a belt buckle. A driving device is disposed within the actuating unit and a ram is telescopically fitted to an upper end of the actuating unit. A chest supporting frame has a center hole defined therein in which an upper end of the ram is received. The chest supporting frame has two connecting portions respectively formed at two sides thereof and a plurality of collars pivotally mounted to both connecting portions. A belt is attached to each collar to enable the chest supporting frame to be secured around the chest by a belt buckle.

The driving device comprises a motor, a screw stem mounted to a lower center of the motor, a gear having one end meshed with the screw stem and the other end meshed to a worm. A worm gear is engaged with the worm and a drive screw stem is attached to an upper end of the worm gear and threadedly engaged with a lower end of the ram.

Further, the drive device also can be manual and includes a screw stem threadedly engaged with a lower end of the ram, a worm gear and a worm meshed with the screw stem. A universal joint is meshed with an outer end of the worm. A rocker is telescopically fitted to the universal joint and a crank is pivotally mounted to an outer end of the rocker.

According to another aspect of the present invention, an apparatus for reforming a spine includes an actuating unit with two recesses respectively defined in each side thereof. Two belts are respectively and securely received in the recess to enable the actuating unit to be secured round the waist by a belt buckle. A driving device is disposed within the actuating unit. A ram is telescopically fitted to an upper end of the actuating unit. A connecting pole is telescopically fitted to an upper end of the ram and a cervix traction pole is fitted to an upper end of the connecting pole and secured to a patient's heed by a belt.

Other objects, advantages, and novel features of the invention will become more apparent from the following detailed description when taken in conjunction with the accompanying drawings.

DESCRIPTION OF THE PREFERRED EMBODIMENT

Figure 1:
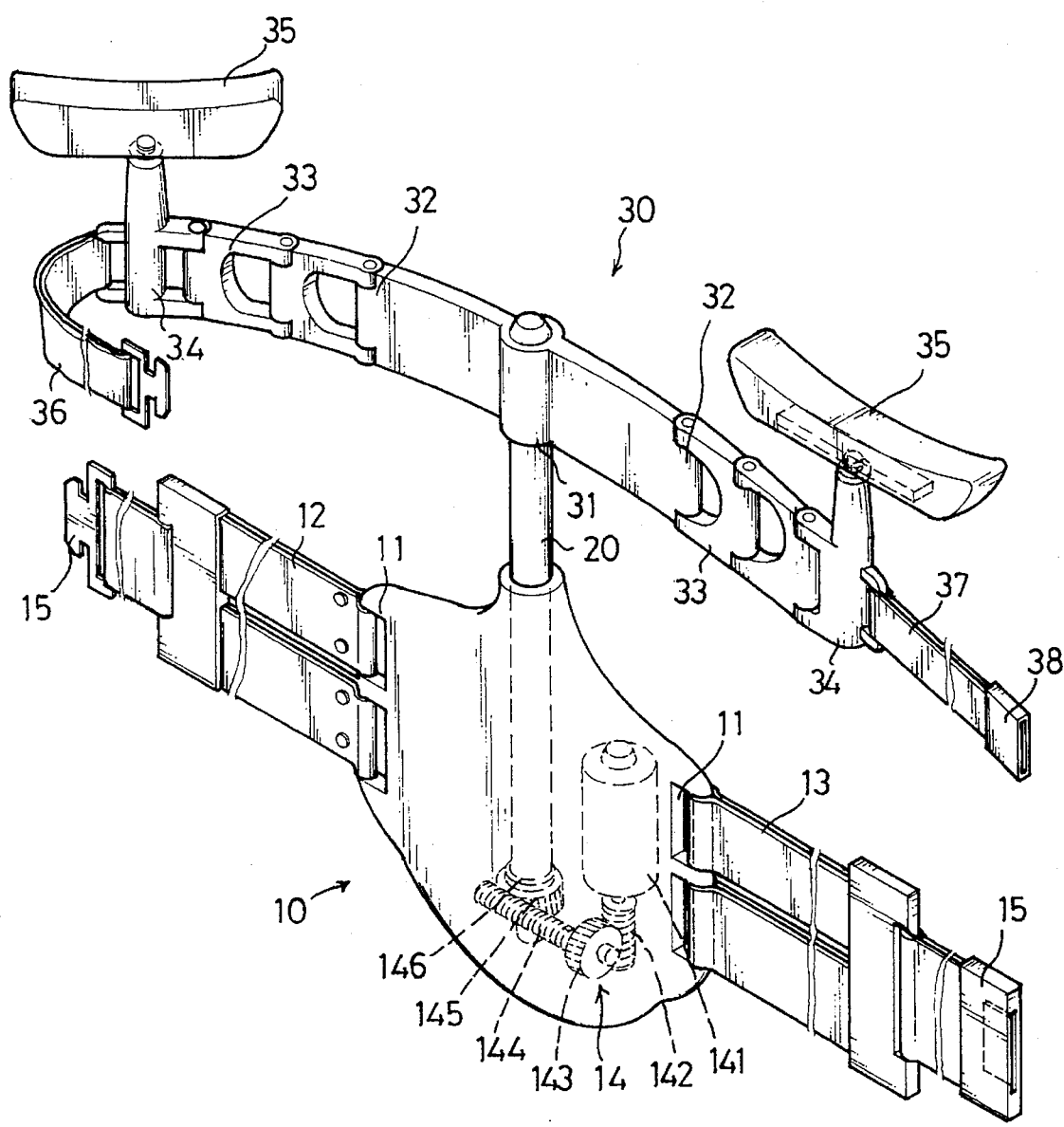
FIG. 1 is a perspective view of an apparatus for reforming a spine in accordance with the present invention.

Referring to the drawings and initially to FIG. 1, an apparatus for reforming a spine comprises an actuating unit 10, a driving device 14 disposed within the actuating unit 10, a ram 20 telescopically fitted to an upper end of the actuating unit 10 and a chest supporting frame 30 attached to an upper end of the ram 20.

Figure 2:
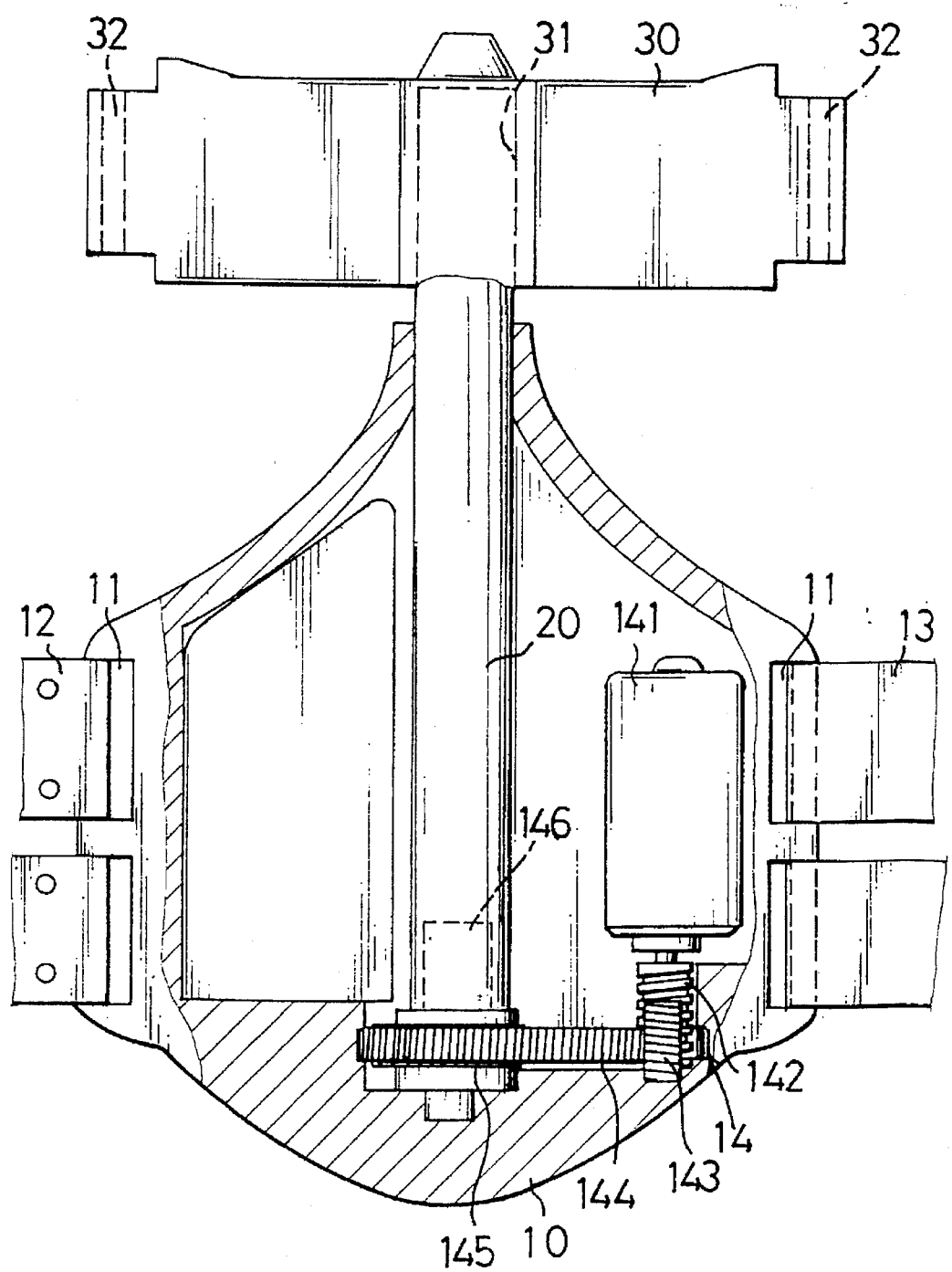
FIG. 2 is a plan view of the apparatus for reforming a spine in accordance with the present invention.
Figure 3:
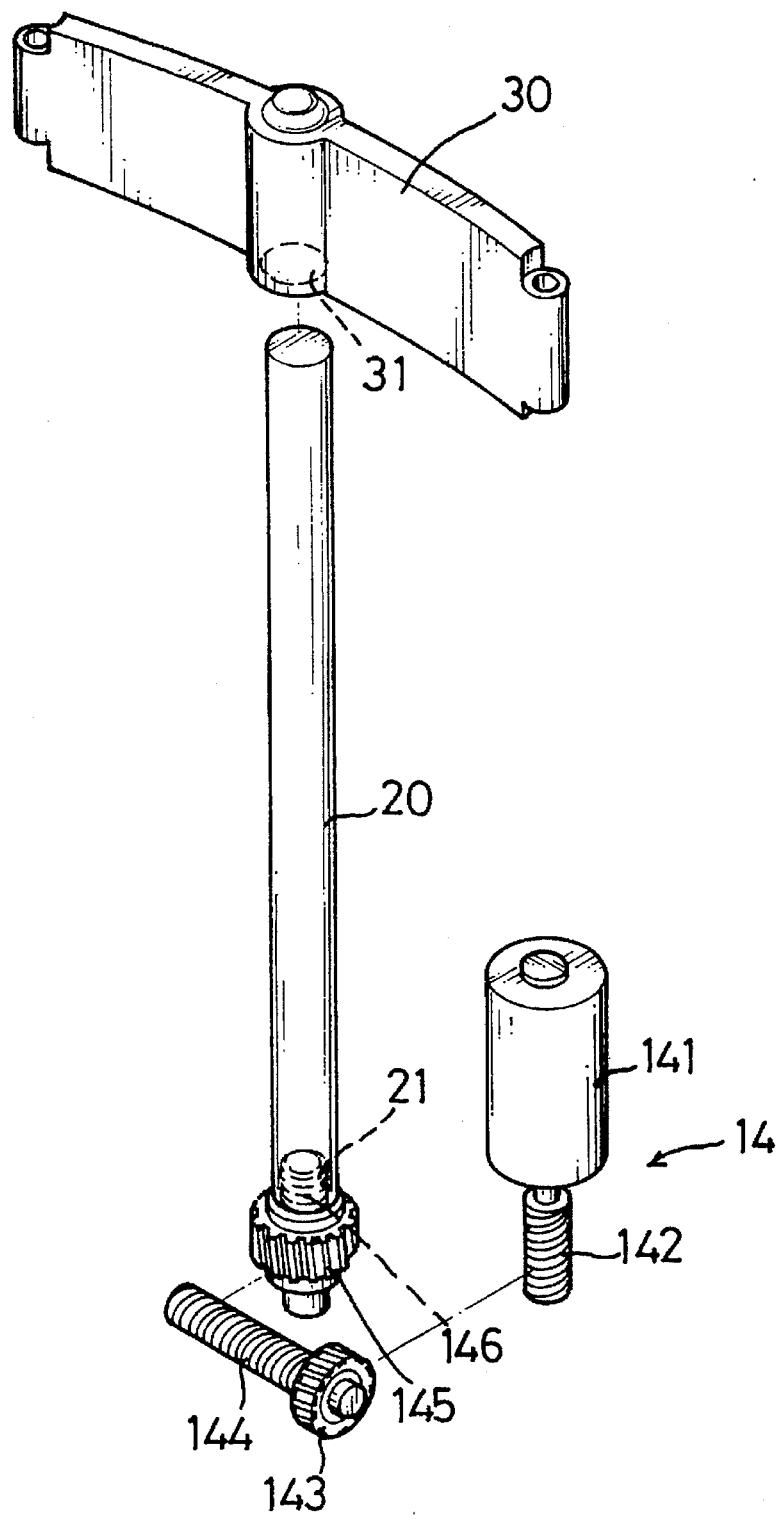
FIG. 3 is a fragmentary exploded view of an electrodynamic driving device of the apparatus in accordance with the present invention.

Still referring to FIG. 1 and further to FIG. 2, the actuating unit 10 is substantially arc-shaped in form with two recesses 11 respectively defined in each side thereof. Two belts 12 and 13 with matched first belt buckles 15 are respectively and securely received in the corresponding recesses 11 and the actuating unit 10 is secured round a patient's waist by the first belt buckles 15 being engaged with each other. The driving device 14 which is electrodynamic is disposed within the inner of the actuating unit 10. Further referring to FIG. 3, the driving device 14 includes a motor 141, a screw stem 142 which is driven by the motor 141 mounted to a lower center of the motor 141, a gear 143 having one end meshed with the screw stem 142 and the other end meshed to a worm 144. A worm gear 145 is engaged with the worm 144 and a drive screw stem 146 is attached to an upper end of the worm gear 145 and threadedly engaged with a lower end of the ram 20. When the motor 141 is actuated, the drive screw stem 146 then can be rotated by means of the screw stem 142, the gear 143, the worm 144 and the worm gear 145. As the bottom of the drive screw stem 146 is in a fixed position, the rotating of the drive screw stem 146 causes the ram 20 to be moved up and down.

Figure 4:
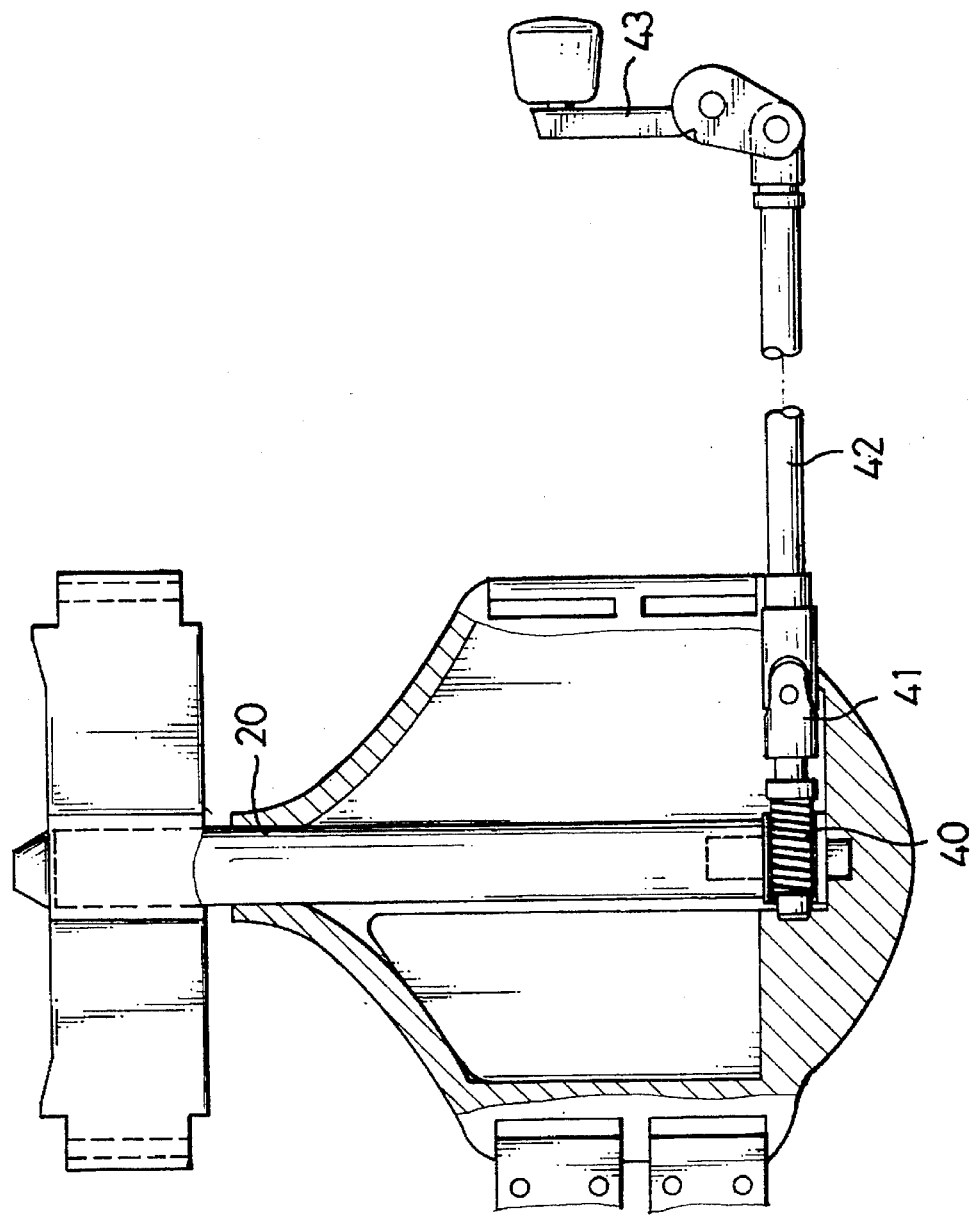
FIG. 4 is a plan view of a manual driving device of the apparatus in accordance with the present invention.

Further, the driving device also can be operated manually. Referring to FIG. 4, the driving device includes a screw stem threadedly engaged with a lower end of the ram 20, a worm gear and a worm 40 meshed with the screw stem. A universal joint 41 is meshed with an outer end of the worm 40. A rocker 42 is telescopically fitted to the universal joint 41 and a crank 43 is pivotally mounted to an outer end of the rocker 42. When the driving device is operated, the rocker 42 is telescopically fitted to the universal joint 41. The ram 20 then can be moved up and down by means of rotating the crank 43.

Figure 6:
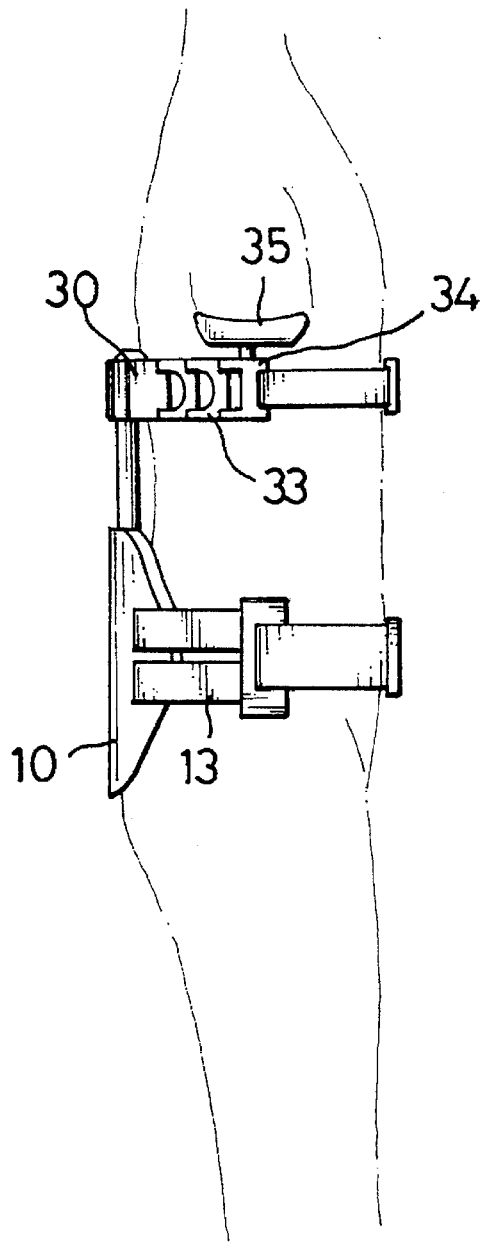
FIG. 6 is a side elevational view showing the apparatus which is used for reforming lumbar vertebrae.
Figure 8:
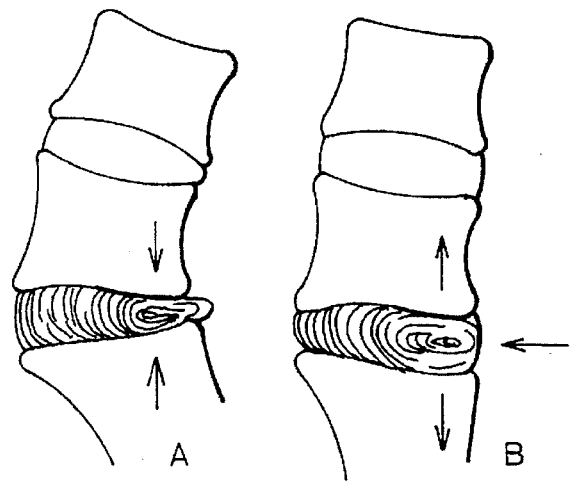
FIG. 8 is a side view of a spine.
Figure 9:
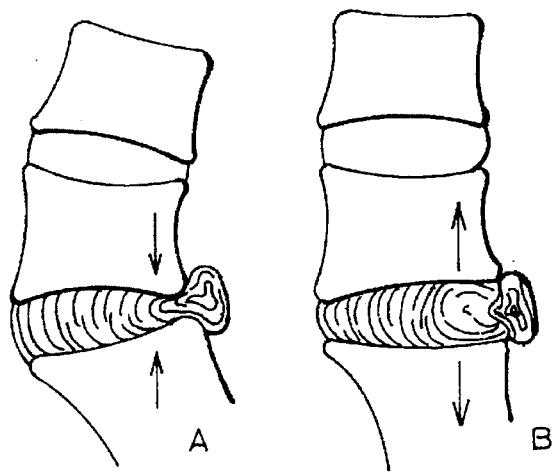
FIG. 9 is another side view of a spine.

Referring to FIGS. 1 and 6, the chest supporting frame 30 is attached to an upper end of the ram 20. The chest supporting frame 30 has a center hole 31 in which the upper end of the ram 20 is received. Two connecting portions 32 are formed at both sides of the chest supporting frame 30. A plurality of collars 33 are pivotally mounted to both connecting portions 32 and two supporting collars 34 are respectively formed at each side of the chest supporting frame corresponding to armpits of the patient. A supporting seat 35 is disposed to an upper end of the supporting collar 34. Additionally, two belts 36 and 37 are attached to each collar to enable the chest supporting frame 30 to be secured round the chest by a second belt buckle 38.

Figure 5:
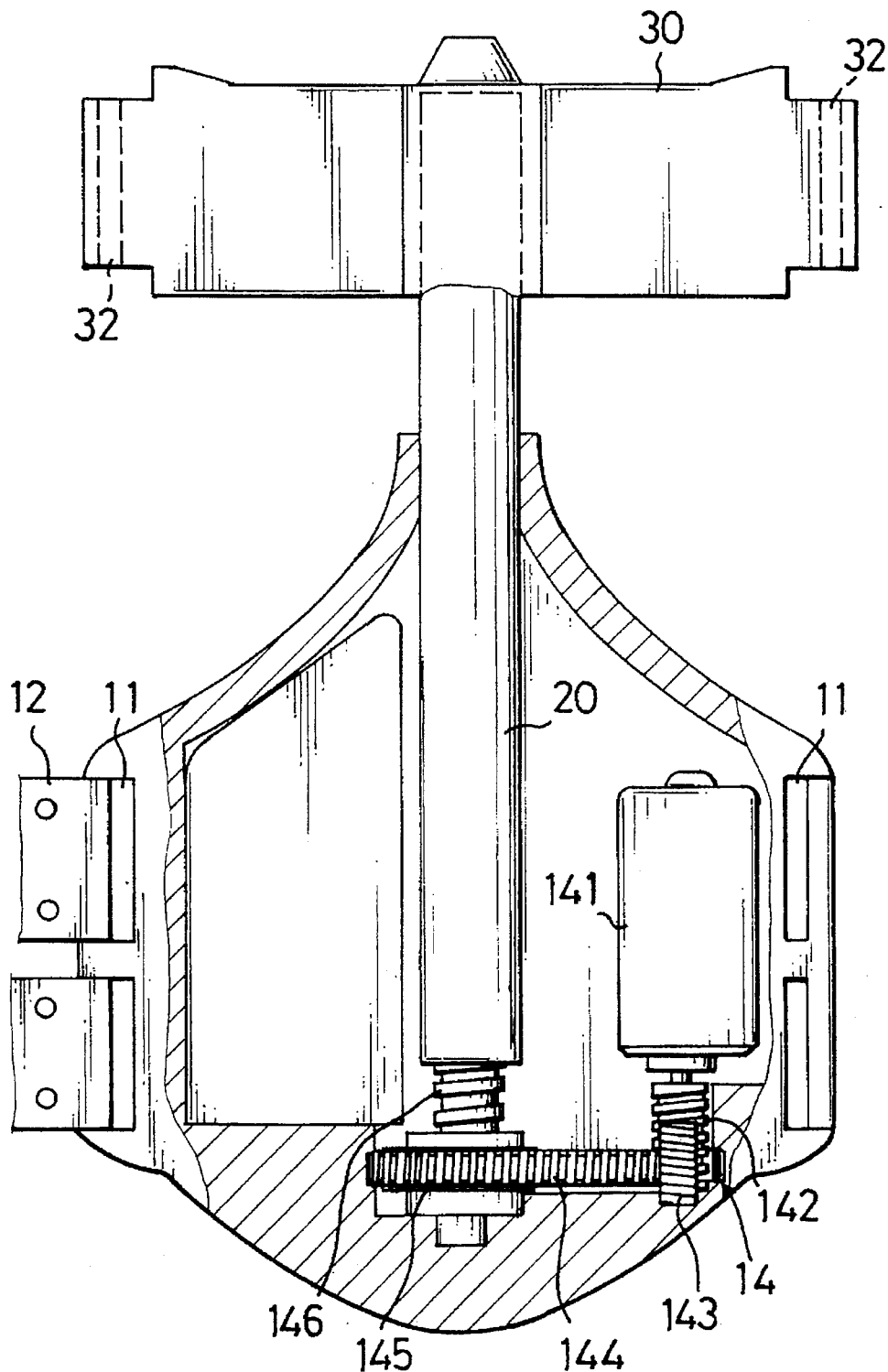
FIG. 5 is a view similar to FIG. 2 showing an action of the apparatus in accordance with the present invention.

As shown in FIGS. 2 and 5, the driving device 14 is rotated forward and reversely whereby the ram 20 is moved up and down, and accordingly, the distance between the chest supporting frame 30 and the actuating unit becomes larger and applies force on the spine to reform the spine.

Figure 7:
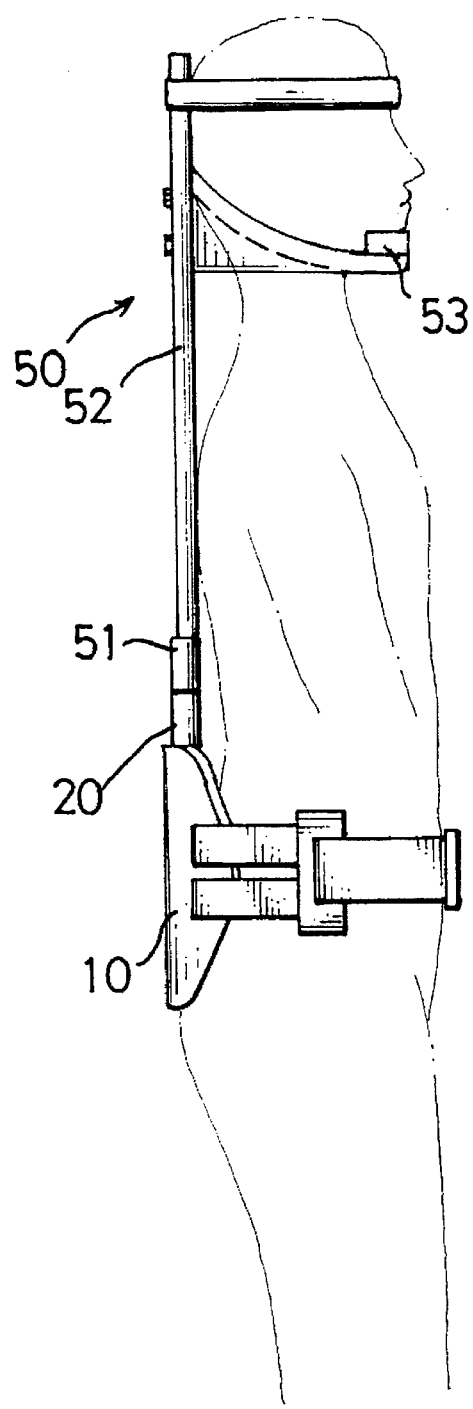
FIG. 7 is a side elevational view showing the apparatus which is used for reforming cervical vertebrae.

As shown in FIG. 7, a cervix traction pole 50, instead of the chest supporting frame 30, is mounted to the ram 20. A connecting pole 51 is telescopically fitted to an upper end of the ram 20 and then the cervix traction pole 50 is fitted to an upper end of the connecting pole 51 and secured to a patient's head by a belt 53, whereby the cervix vertebrae can be drawn and reformed. The length of the connecting pole 51 is discretionary to be adapted to anyone.

From the foregoing, it is seen that the objects hereinbefore set forth may readily and efficiently be attained, and since certain changes may be made in the above construction and different embodiments of the invention without departing from the scope thereof, it is intended that all matter contained in the above description or shown in the accompanying drawings shall be interpreted as illustrative and not in a limiting sense.

What is claimed is:

1. An apparatus for reforming a spine, comprising:

an actuating unit with two recesses respectively defined in each side thereof, two belts respectively and securely received in the recesses to enable the actuating unit to be secured around a patient's waist by a belt buckle;

a driving device disposed within the actuating unit;

a ram attached to the driving device and telescopically fitted to an upper end of the actuating unit; and a chest supporting frame defining a center hole in which an upper end of the ram is received, the chest supporting frame having two connecting portions respectively formed at both sides thereof and a plurality of collars pivotally mounted to each of the connecting portions, a belt attached to an end collar of each said plurality of collars to enable the chest supporting frame to be secured around the chest by a belt buckle.

2. The apparatus in accordance with claim 1, wherein the driving device is electrodynamic and comprises a motor; a screw stem mounted to a lower center of the motor; a gear having one end meshed with the screw stem and the other end meshed to a worm; a worm gear engaged with the worm; and a drive screw stem attached to an upper end of the worm gear and threadedly engaged with a lower end of the ram.

3. The apparatus in accordance with claim 1, wherein the drive device is manually operable and comprises a screw stem threadedly engaged with a lower end of the ram; a worm gear and a worm meshed with the screw stem; a universal joint meshed with an outer end of the worm; a rocker telescopically fitted to the universal joint; and a crank pivotally mounted to an outer end of the rocker.

4. The apparatus in accordance with claim 1, wherein the chest supporting frame further includes a supporting collar formed at each side corresponding to the patient's armpits and a supporting seat disposed to an upper end of the supporting collar.

5. The apparatus in accordance with claim 4, wherein the supporting seat is threadedly engaged with the supporting collar so that the supporting seat can move with respect to the supporting collar.

\* \* \* \* \*